(12) United States Patent
Güthner et al.

(10) Patent No.: US 11,512,047 B2
(45) Date of Patent: Nov. 29, 2022

(54) METASTABLE CRYSTAL MODIFICATION AND METHOD FOR PRODUCING THE SAME (I)

(71) Applicant: Alzchem Trostberg GmbH, Trostberg (DE)

(72) Inventors: Thomas Güthner, Trostberg (DE); Franz Thalhammer, Trostberg (DE); Jürgen Sans, Trostberg (DE)

(73) Assignee: Alzchem Trostberg GmbH, Trostberg (DE)

(*) Notice: Subject to any disclaimer, the term of this patent is extended or adjusted under 35 U.S.C. 154(b) by 0 days.

(21) Appl. No.: 17/625,494

(22) PCT Filed: Jun. 25, 2020

(86) PCT No.: PCT/EP2020/067837
§ 371 (c)(1),
(2) Date: Jan. 7, 2022

(87) PCT Pub. No.: WO2021/008843
PCT Pub. Date: Jan. 21, 2021

(65) Prior Publication Data
US 2022/0204443 A1 Jun. 30, 2022

(30) Foreign Application Priority Data
Jul. 12, 2019 (DE) .............. 10 2019 118 893.8
Jul. 12, 2019 (DE) .............. 10 2019 118 894.6

(51) Int. Cl.
*C07C 279/14* (2006.01)

(52) U.S. Cl.
CPC ........ *C07C 279/14* (2013.01); *C07B 2200/13* (2013.01)

(58) Field of Classification Search
CPC ... C07C 277/08; C07C 279/04; C07C 279/14; C07B 2200/13
See application file for complete search history.

(56) References Cited

U.S. PATENT DOCUMENTS

| | | | |
|---|---|---|---|
| 2,620,354 A | 12/1952 | Vassel et al. | |
| 2,654,779 A | 10/1953 | Vassel et al. | |
| 2010/0055182 A1 | 3/2010 | Gastner et al. | |

FOREIGN PATENT DOCUMENTS

| | | |
|---|---|---|
| CN | 101525305 A | 9/2009 |
| CN | 106361736 A | 2/2017 |
| DE | 964590 C | 5/1957 |
| DE | 102007004781 A1 | 8/2008 |
| DE | 102007053369 A1 | 7/2009 |
| JP | 60054320 A | 3/1985 |
| WO | 2000059528 A1 | 10/2000 |
| WO | 2005120246 A1 | 12/2005 |
| WO | 2008092591 A2 | 8/2008 |
| WO | 2009012960 A2 | 1/2009 |

OTHER PUBLICATIONS

Guha, "The Crystal and Molecular Structure of Glycocyamine", Acta Crystallographica, vol. 29, No. 10, Oct. 1, 1973, pp. 2163-2166.
Jones et al., "Conformations of GABA Analogues. I: Crystal and Molecular Structure of Guanidinoacetic Acid", Journal of Crystal and Molecular Structure, vol. 9, No. 5, Oct. 1, 1979, pp. 273-279.
Singh et al., "Determination of formation constants of some mixed complexes of glycocymin and Nitrilotriacetic acid by paper electrophoresis (Cu(II), UO2(II), Co(II), Zn(II), Cd(II)-Nitrilotriacetic acid-Glycocymin System)", Oriental Journal of Chemistry, vol. 24(1), 2008, pp. 283-286.
International Application No. Application No. PCT/EP2020/067837, International Search Report and Written Opinion, dated Jul. 31, 2020, 13 pages.
German Application No. 10 2019 118 894.6, German Search Report dated Jul. 2, 2020, 7 pages.
German Application No. 10 2019 118 893.8, German Search Report dated Jul. 2, 2020, 7 pages.
Strecker, M., "Organische Chemie. and Organische Basen", 1861, pp. 530-531.
Berthou et al., "Structure Cristalline et Moleculaire de la Glycocyamine", Acta Crystallographica, vol. B32, 1976, pp. 1529-1532.
De Miranda et al., "Study on Guanidino-Carboxylate Interactions in Copper(II) Ternary Complexes of Guanidinoacetic Acid with Glutamic and Aspartic Acids", Polyhedron, vol. 22, Issue 2, Jan. 15, 2003, pp. 225-233.
German Application No. DE102019118893.8, Search Report dated Feb. 7, 2020, 7 pages.
German Application No. DE102019118894.6, Search Report dated Feb. 7, 2020, 7 pages.
Du et al., "Self-Antibacterial UV-Curable Waterborne Polyurethane with Pendant Amine and Modified by Guanidinoacetic Acid", Journal of Materials Science, vol. 53, No. 1, Jan. 2018, pp. 215-229.
International Application No. PCT/EP2020/067842, International Preliminary Reporton Patentability dated Nov. 30, 2021, 6 pages.
International Application No. PCT/EP2020/067839, International Search Report and Written Opinion dated Jan. 21, 2021, 7 pages.
Wang et al., "Solid State Studies of the Assembly of Diionic Guanidinium/Carboxylate Compounds", Tetrahedron Letters, vol. 56, No. 21, May 20, 2015, pp. 2684-2687.
International Application No. PCT/EP2020/067842, International Search Report and Written Opinion dated Jan. 21, 2021, 9 pages.
International Application No. PCT/EP2020/067837, International Preliminary Report on Patentability dated Jan. 27, 2022, 8 pages.
International Application No. PCT/EP2020/067839, International Preliminary Report on Patentability dated Jan. 5, 2022, 7 pages.

*Primary Examiner* — Susanna Moore
(74) *Attorney, Agent, or Firm* — Kilpatrick Townsend & Stockton LLP (57) ABSTRACT

The present invention relates to a new crystal modification of N-(aminoiminomethyl)-2-aminoacetic acid as well as a method for producing this crystal modification.

12 Claims, 5 Drawing Sheets

METASTABLE CRYSTAL MODIFICATION AND METHOD FOR PRODUCING THE SAME (I)

CROSS REFERENCE TO RELATED APPLICATION

This application is a U.S. national phase of International Patent Application No. PCT/EP2020/067837 filed on Jun. 25, 2020, which claims priority to German Patent Application Nos. 10 2019 118 894.6 and 10 2019 118 893.8, both filed in Germany on Jul. 12, 2019. The entire contents of all applications are hereby incorporated herein by this reference.

The present invention relates to a new crystal modification of N-(aminoiminomethyl)-2-aminoacetic acid as well as a method for producing this crystal modification.

N-(aminoiminomethyl)-2-aminoacetic acid (CAS no. 352-97-6, molecular formula $C_3H_7N_3O_2$), also known as guanidinoacetic acid, guanidinoacetate, glycocyamine, N-amidinoglycine or N-(aminoiminomethyl)-glycine, is a guanidinocarboxylic acid with many uses, amongst others for the synthesis of chemical products, in particular pharmaceuticals (cf. WO 2000/059528), for the direct use as a pharmaceutical active substance in renal diseases (cf. JP 60054320) or neurodegenerative diseases (cf. CN 106361736), in the manufacture of polymers (cf. Du, Shuo et. al., Journal of Materials Science (2018), 53(1), 215-229), as a complexing agent for metals (cf. Lopes de Miranda et. al., Polyhedron (2003), 22(2), 225-233 or Singh, Padmakshi et. al, Oriental Journal of Chemistry (2008), 24(1), 283-286) and as an additive for feeding animals, in particular mammals, fish, birds (cf. WO 2005/120246) and humans (cf. WO 2008/092591, DE 102007053369).

N-(aminoiminomethyl)-2-aminoacetic acid can for example be produced from glycine through conversion with cyanamide according to Strecker, M. (Jahresber. Fortschr. Chem. Verw. (1861), 530). Alternatively N-(aminoiminomethyl)-2-aminoacetic acid can for example be produced through conversion of glycine with S-methylisothiourea-iodide using potassium hydroxide as a base (cf. U.S. Pat. No. 2,654,779). The conversion of chloroacetic acid with ammonia into glycine hydrochloride and its further conversion with cyanamide has also been described (cf. U.S. Pat. No. 2,620,354).

The conversion of cyanamide with glycine into glycocyamine at a pH value of 9 to 10 was described in DE 964 590.

With the known methods N-(aminoiminomethyl)-2-aminoacetic acid is produced as a fine crystalline powder, which has a substantial dust content, i.e. a substantial proportion of particles with a grain size of less than 63 μm.

It is often desirable when handling chemical products in a solid form that these are present in a crystalline, grainy, flowable, dust-free form without, or with just a low fine grain content. A poorly flowable, dusty powder is completely unsuitable for use as an animal feed additive.

In order to address this situation it has for example been suggested to transform N-(aminoiminomethyl)-2-aminoacetic acid by adding polymer binding agents (for example methylcellulose) in quantities of 0.05 to 15 wt. % and by adding water into preforms, granulates or extrudates (cf. WO 2009/012960). One disadvantage of this method is that adding a foreign material, namely a binding agent, is essential, and that the preforms must be produced during an additional method step using a special, technically complex and expensive apparatus such as for example an extruder, granulator, intensive mixer or plough blade mixer, with subsequent drying of the granulate or the preforms.

It is also a disadvantage of the method according to above prior art that preforms or granulates either have a high binding agent content, and therefore a low dissolution rate, or dissolve relatively quickly with a low binding agent content, but at the same time have low firmness and high wear value, so that a freedom from dust can no longer be guaranteed.

The invention is based on the problem of providing N-(aminoiminomethyl)-2-aminoacetic acid in the form of flowable, non-dusty crystal aggregates that do not have the disadvantages of prior art, but can be produced easily and with widespread standard apparatuses of the chemical industry, and which also have high solubility. A suitable method for producing these crystal aggregates is also to be provided.

These problems are solved by a thermodynamically metastable crystal modification according to claim 1 as well as a method for producing the same according to claim 7. Preferred embodiments of the invention are listed in the subclaims, which can be optionally combined with each other.

The occurrence of chemical substances in various crystal forms or crystal modifications (polymorphism) is of great importance for the manufacture and use of the substances as well as for the development of formulations. The various crystal modifications of a chemical compound therefore differ in numerous further physical or physico-chemical properties in addition to their appearance (crystal habit). It has not been possible to date to predict the occurrence and the number of crystal modifications including their physical or physico-chemical properties. The thermodynamic stability in particular, also the different behaviour following administration to living organisms cannot be determined in advance.

Under given pressure and temperature conditions the various polymorphic crystal modifications usually have different lattice energies or standard heats of formation. The crystal form with the lowest energy is designated as stable form. Forms with higher energetic positions are designated as metastable, if they can be isolated (under the given pressure and temperature conditions). Metastable polymorphs have the tendency to convert into the stable polymorph. Because of the metastability this requires the exertion of activation energy, for example through the effect of heat, mechanical energy or the influence of a solvent.

It is also generally known that the various modifications of a substance can be present monotropically or enantiotropically. In the case of the monotropic polymorphism a crystal form or crystal modification can constitute the thermodynamically stable phase across the entire temperature range up to the melting point, whilst a conversion point exists with enantiotropic systems, where the stability behaviour is reversed.

A thermodynamically metastable crystal modification of N-(aminoiminomethyl)-2-aminoacetic acid not known to date has now surprisingly been found. According to a first embodiment of the present invention a thermodynamically metastable crystal modification of N-(aminoiminomethyl)-2-aminoacetic acid is therefore the subject of the present invention, which displays the strongest reflex bands at 2Θ (2 theta)=20.2° and 23.3° and 23.8° and 25.3° at a measuring accuracy of +/−0.2° in the x-ray powder diffractogram of the crystal modification when using Cu-Kα$_1$ radiation. Cu-Kα$_1$ radiation means a copper K-alpha-1 radiation with a wavelength of 1.5406 Å here and hereafter, as is normally utilised during crystallographic studies.

Figure 2:
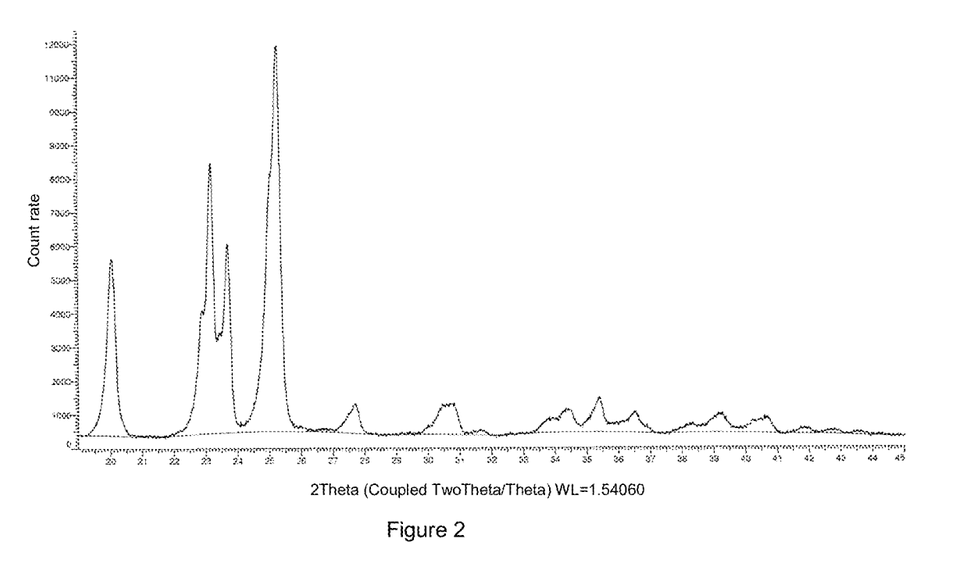
FIG. 2: an x-ray powder diffractogram of N-(aminoiminomethyl)-2-aminoacetic acid of the form B from example 2.

The thermodynamically metastable crystal modification of N-(aminoiminomethyl)-2-aminoacetic acid according to the invention preferably has an x-ray powder diffractogram when using Cu-K$\alpha_1$ radiation as illustrated in FIG. 2.

A thermodynamically metastable crystal modification of N-(aminoiminomethyl)-2-aminoacetic acid, which has the orthorhombic space group P2$_1$2$_1$2$_1$ with Z=8 with the lattice constants a=7.7685 Å, b=7.7683 Å, c=17.4261 Å at a measuring accuracy of +/−0.001 Å is preferred. The single crystal measurement is here carried out with a Mo-K$\alpha$ radiation with the wavelength 0.71073 Å at 105 K (Kelvin). The elementary cell volume is 1052 Å$^3$ and the calculated x-ray crystal density 1.479 g/cm$^3$ at 105 Kelvin.

Also preferred is a thermodynamically metastable crystal modification of N-(aminoiminomethyl)-2-aminoacetic acid, which crystallises in the orthorhombic, polar space group P2$_1$2$_1$2$_1$ with Z=8, i.e. with two crystallographically independent molecules, and which has a pseudo-tetragonal packaging. The elementary cell has the lattice constants a=7.7685 Å, b=7.7683 Å, c=17.4261 Å at a measuring accuracy of +/−0.001 Å at 105 Kelvin. The single crystal measurement was here carried out with a Mo-K$\alpha$ radiation with a wavelength 0.71073 Å. The elementary cell volume is 1052 Å$^3$ and the calculated x-ray crystal density 1.479 g/cm$^3$ at 105 Kelvin.

According to the present invention an orthorhombic space group is a space group, the elementary cell of which has three right angles (right angle=90°) and the 3 crystal axes a, b and c of which have different lengths.

According to a preferred embodiment a thermodynamically metastable crystal modification of N-(aminoiminomethyl)-2-aminoacetic acid is therefore also subject of the present invention, which shows the strongest reflex bands at 2$\Theta$=20.2° and 23.3° and 23.8° and 25.3° at a measuring accuracy of +/−0.2° in the x-ray powder diffractogram of the crystal modification when using Cu-K$\alpha$, radiation, which crystallises in the orthorhombic, polar space group P2$_1$2$_1$2$_1$ with two crystallographically independent molecules, i.e. Z=8, and which has a pseudo-tetragonal packaging. The elementary cell has the lattice constants a=7.7685 Å, b=7.7683 Å, c=17.4261 Å at a measuring accuracy of +/−0.001 Å at 105 Kelvin.

The crystal modification also preferably has a cell volume of 1052 Å$^3$ and an x-ray crystal density of 1.479 g/cm$^3$ at 105 Kelvin.

It was found as part of the present invention that N-(aminoiminomethyl)-2-aminoacetic acid also occurs in a thermodynamically metastable crystal modification in addition to the already known thermodynamically stabile crystal modification (hereafter also called form A or crystal form A). This thermodynamically metastable crystal form according to the invention is hereafter also called form B or crystal form B.

This new crystal form B forms under suitable crystallisation conditions polygonal or spherical, radially radiating aggregates made of needle-shaped part-crystallites, which have a rounded habitus and a mostly consistent aggregate size. As a solid they therefore ensure optimal handling in that they enable a dust-free, easily flowable product without packing tendencies. The crystal modification B can be classed as low-dust, as the proportion of crystals with a grain size of <63 μm (mesh size) lies below 10%, preferably below 5%. Thanks to its construction from fine, needle-shaped part-crystallites this habitus of the new crystal form B of N-(aminoiminomethyl)-2-aminoacetic acid also ensures a higher dissolution rate. In addition, and completely unexpectedly, N-(aminoiminomethyl)-2-aminoacetic acid of the crystal form B also offers a higher absolute solubility in aqueous media.

The metastable crystal modification of N-(aminoiminomethyl)-2-aminoacetic acid according to the invention preferably exists in a pure form. At least 50 wt. %, more preferably at least 75 wt. %, still more preferably at least 90 wt. %, in particular at least 95 wt. %, and most preferably at least 99 wt. % of the N-(aminoiminomethyl)-2-aminoacetic acid in a composition preferably have a crystal modification in the x-ray powder diffractogram when using Cu-K$\alpha_1$ radiation with the strongest reflex bands of 2$\Theta$=20.2.° and 23.3° and 23.8° and 25.3° at a measuring accuracy of +/−0.2.

Figure 1:
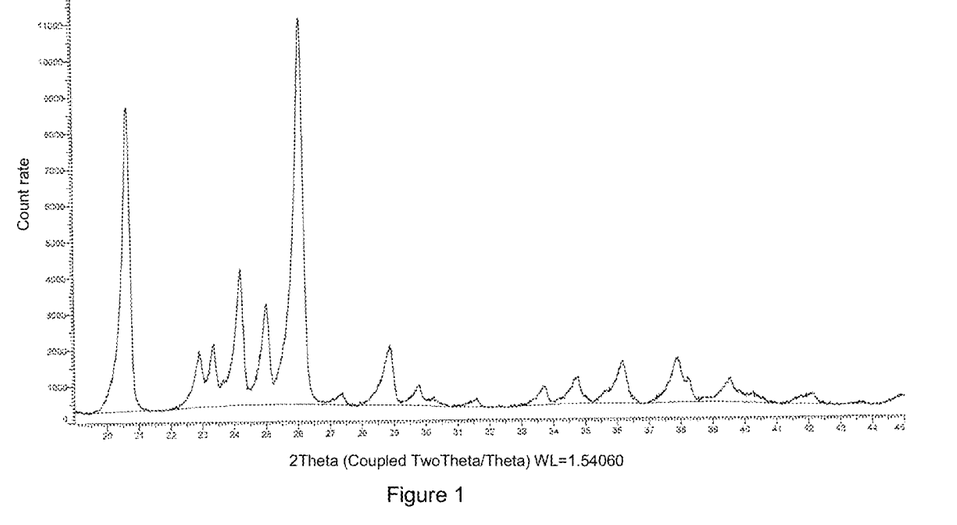
FIG. 1: An x-ray powder diffractogram of N-(aminoiminomethyl)-2-aminoacetic acid of the form A from example 1.

If N-(aminoiminomethyl)-2-aminoacetic acid is produced according to one of the known methods, in particular from aqueous reaction mixtures, the compound occurs in the well-known crystal form A. One and the same crystal structure has been described by three groups of authors: by Sankarananda Guha, Acta Cryst. B29 (1973), 2163 or by Par J. Berthou et al., Acta Cryst B32 (1976), 1529 and by Wei Wang et al., Tetrahedron Letters 56 (2015), 2684. All three works describe N-(aminoiminomethyl)-2-aminoacetic acid (here called form A) as a monoclinic structure of the space group P21/n with Z=4 and the approximated lattice constants a=4.95 Å, b=6.00 Å, c=17.2 Å, β=94.5°, with a cell volume of approx. 510 Å$^3$, wherein the published space group P2$_1$/c was transferred into space group P2$_1$/n by means of coordinate transformation in Berthou et al. The experimental crystal density of N-(aminoiminomethyl)-2-aminoacetic acid of the form A is approx. 1.50 g/cm$^3$. The characteristic powder diffractogram of N-(aminoiminomethyl)-2-aminoacetic acid in form A is shown in FIG. 1. Using Cu-K$\alpha_1$ radiation (copper K-alpha-1 radiation), in particular the band positions 2$\Theta$ (2 theta)=20.6° and 26.0° are characteristic for form A. The powder diffractogram is in agreement with the diffraction pattern calculated from the published single crystal structures.

If N-(aminoiminomethyl)-2-aminoacetic acid is recrystallised from usual solvents such as for example water, methanol, ethanol, isopropanol or mixtures of methanol, ethanol, ethandiol or acetonitrile with water, or is produced therein, then N-(aminoiminomethyl)-2-aminoacetic acid occurs only in crystal form A, as has been shown during trials.

It has been found in a completely surprising way that N-(aminoiminomethyl)-2-aminoacetic acid crystallises from a calcium chloride-containing solution, in particular an aqueous calcium chloride solution, with a calcium chloride proportion of 5 to 50 wt. %, especially with a calcium chloride proportion of 10 to 40 wt. %, in a new, as yet unknown crystal form.

N-(aminoiminomethyl)-2-aminoacetic acid of the form B is characterised by its powder diffractogram with Cu-K$\alpha_1$ radiation (see FIG. 2), wherein the bands are characteristic at 2$\Theta$ (2 theta)=20.2° and 25.3° and a weaker double reflex at 2$\Theta$ (2theta)=23.3°/23.8°. A single crystal x-ray structure analysis resulted for N-(aminoiminomethyl)-2-aminoacetic acid of the form B in the orthorhombic, polar space group P2$_1$2$_1$2$_1$ with two crystallographically independent molecules, i.e. Z=8. The packaging of the molecules has a pseudo-tetragonal symmetry. The elementary cell has the lattice constants a=7.7685 Å, b=7.7683 Å, c=17.4261 Å at a measuring accuracy of +/−0.001 Å at 105 Kelvin. The single crystal measurement was here carried out with a Mo-K$\alpha$ radiation with the wavelength 0.71073 Å. The elementary cell volume is 1052 Å$^3$ and the calculated x-ray crystal density 1.479 g/cm$^3$ at 105 Kelvin.

According to a further embodiment a thermodynamically metastable crystal modification of N-(aminoiminomethyl)-2-aminoacetic acid is therefore also a subject of the present invention, which crystallises in an orthorhombic space group $P2_12_12_1$, in particular an orthorhombic, polar space group $P2_12_12_1$, with Z=8, and which in particular has a pseudo-tetragonal packaging. The elementary cell has the lattice constants a=7.7685 Å, b=7.7683 Å, c=17.4261 Å at a measuring accuracy of +/−0.001 Å at 105 Kelvin.

The experimental crystal density of N-(aminoiminomethyl)-2-aminoacetic acid of the form B is 1.41 g/cm$^3$+/−0.03 g/cm$^3$ at 20° C. The experimental crystal density of form B thus lies clearly below that of crystal form A, which is 1.50 g/cm$^3$+/−0.03 g/cm$^3$ at 20° C. This difference in the crystal density indicates a thermodynamic instability of form B compared to form A.

A thermodynamically metastable crystal modification is therefore preferably also a subject of the invention, which has an experimental crystal density of 1.41 g/cm$^3$+/−0.03 g/cm$^3$ at 20° C.

Figure 3:
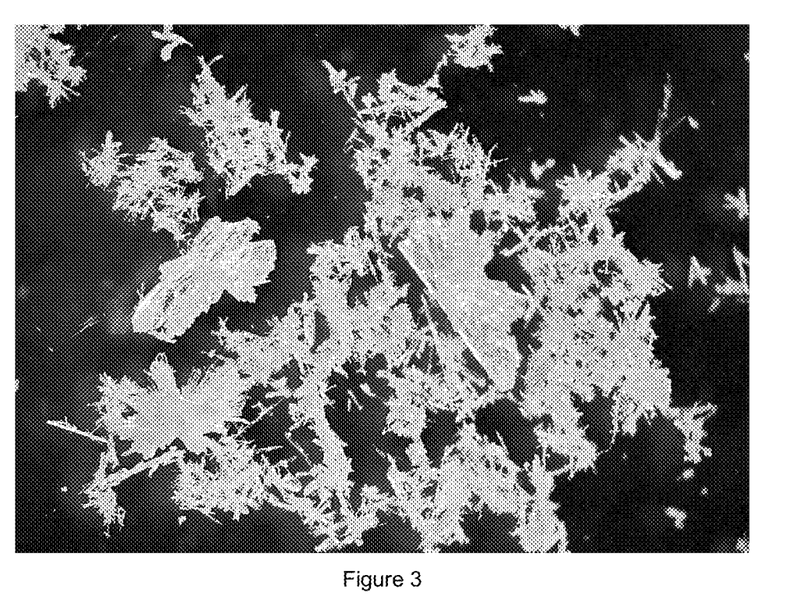
FIG. 3: a microphotography of N-(aminoiminomethyl)-2-aminoacetic acid of the form A, produced according to example 1 (image width 8 mm)
Figure 4:
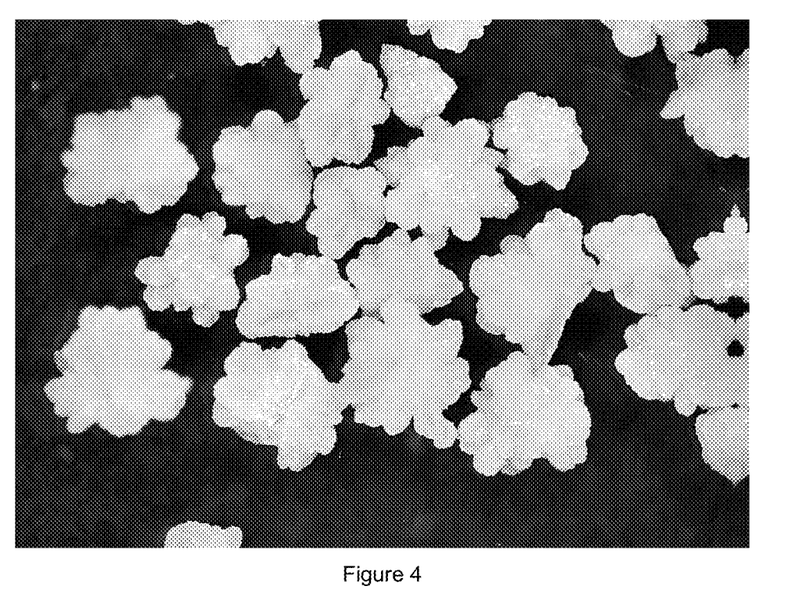
FIG. 4: a microphotography of polygonal aggregates of N-(aminoiminomethyl)-2-aminoacetic acid of the form B, produced through recrystallisation from a 30% aqueous calcium chloride solution according to example 2 (image width 8 mm)
Figure 5:
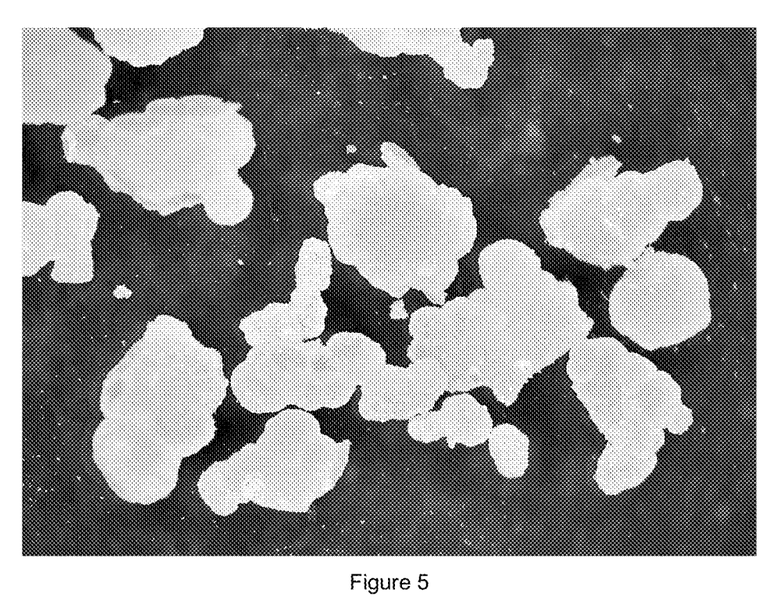
FIG. 5: a microphotography of spherical aggregates of N-(aminoiminomethyl)-2-aminoacetic acid of the form B, produced through recrystallisation from a 15% aqueous calcium chloride solution according to example 3 (image width 8 mm)

Crystal form B of N-(aminoiminomethyl)-2-aminoacetic acid preferably exists in the form of spherical or polygonal, radially radiating aggregates with an externally rounded habitus. The single crystals constitute very fine needles, of which the spherical aggregates are constructed. This has the surprising advantage that a physical form of N-(aminoiminomethyl)-2-aminoacetic acid can be provided by means of form B, which comprises spherical or polygonal, grainy, wear-resistant aggregates with a mostly consistent aggregate size, an excellent pourability and which is mostly dust-free. Typical crystal aggregates of N-(aminoiminomethyl)-2-aminoacetic acid of the form B are shown in FIG. 4 and FIG. 5. A conventional N-(aminoiminomethyl)-2-aminoacetic acid of the form A corresponding to prior art, which has the habitus of matted, fine crystal needles, is shown for comparison in FIG. 3.

N-(aminoiminomethyl)-2-aminoacetic acid of form A and form B also differ in their infrared spectrum. Stronger bands at 1005.9, 940.3 and 816.8 cm$^{-1}$ are characteristic for form A, whilst stronger bands at 1148.0, 997.7 and just a weak band at 815 cm$^{-1}$ are characteristic for form B.

The two crystal forms show different melting or decomposition points: N-(aminoiminomethyl)-2-aminoacetic acid of form A: DSC onset 280.5° C., peak 286.3° C., melt heat 887+/−1 J/g.

N-(aminoiminomethyl)-2-aminoacetic acid of form B: DSC onset 272.5° C., peak 280.4° C., melt heat 860+/−1 J/g.

A thermodynamically metastable crystal modification is therefore preferably also a subject of the invention, which has endothermic melt heat within a range of 850 to 870 J/g.

A thermodynamically metastable crystal modification is therefore also preferably a subject of the invention, which has a decomposition point within a range of 270 to 275° C.

These data impressively show that N-(aminoiminomethyl)-2-aminoacetic acid form B is a thermodynamically metastable crystal modification that constitutes the thermodynamically more unstable form compared to form A, wherein the energy difference between the two forms is approx. 27 J/g, and wherein the starting point of the melting ranges (onset) shows a difference of 8 K.

Figure 6:
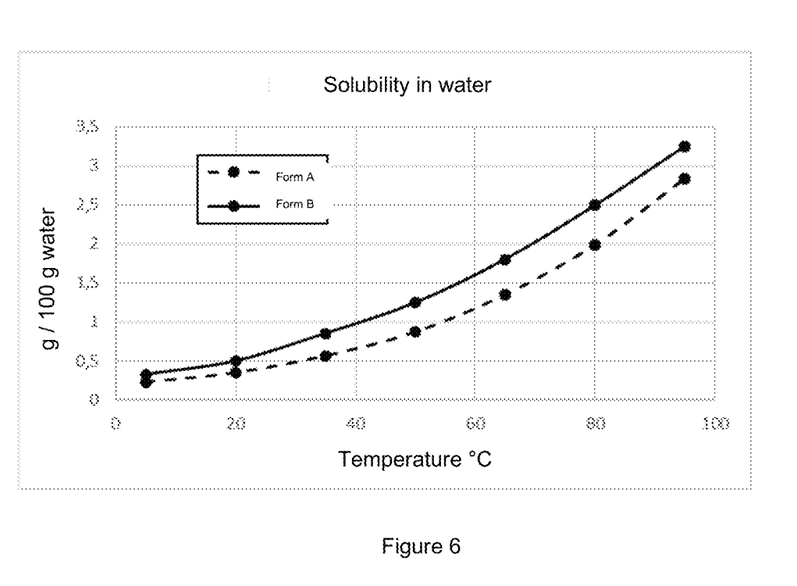
FIG. 6: a solubility graph of N-(aminoiminomethyl)-2-aminoacetic acid of the form A or form B, respectively, in water.

Further investigations have shown that N-(aminoiminomethyl)-2-aminoacetic acid of form B has a water solubility that is approx. 20% higher than that of N-(aminoiminomethyl)-2-aminoacetic acid of form A, and that this fact applies for a temperature range of between 5 and 95° C. (compare FIG. 6). This effect is completely unexpected.

It was found that the metastable crystal modification of form B according to the invention is stable up to its melting point. A solids transformation of form B into form A or a reversible solids transformation form A/form B was not observed. Form B thus represents an example for a monotropic polymorphy.

In summary it should be noted here that N-(aminoiminomethyl)-2-aminoacetic acid in the crystal modification B, in particular produced through crystallisation of N-(aminoiminomethyl)-2-aminoacetic acid from a calcium chloride-containing, preferably aqueous or water-containing solution, combines surprisingly advantageous, and normally mutually exclusive properties, such as for example a coarse, flowable grain and simultaneously a high dissolution rate, the formation of crystal aggregates without adding a binding agent, and provides an increased absolute solubility at a given temperature despite an identical chemical composition.

Thanks to its excellent properties this new crystal modification is suitable for use as a feed additive for animals. A feed additive comprising the thermodynamically metastable crystal modification of N-(aminoiminomethyl)-2-aminoacetic acid described herein is therefore also a subject of the present invention.

A feed additive comprising a thermo-dynamically metastable crystal modification of N-(aminoiminomethyl)-2-aminoacetic acid is therefore in particular also a subject of the present invention, the x-ray powder diffractogram of which, when using Cu-K$\alpha_1$ radiation, displays the strongest reflex bands at 2Θ=20.2° and 23.3° and 23.8° and 25.3° at a measuring accuracy of +/−0.2°.

Very particularly preferred is a feed additive comprising a thermodynamically metastable crystal modification of N-(aminoiminomethyl)-2-aminoacetic acid, which comprises no binding agents or which is free from the binding agents normally used for granulation.

Such feed additives can be formulated as premixes. The use of the thermodynamically metastable crystal modification of N-(aminoiminomethyl)-2-aminoacetic acid described herein for producing a feed additive is therefore also a subject of the invention.

It has surprisingly been found that N-(aminoiminomethyl)-2-aminoacetic acid can be present in different crystal modifications. The thermodynamically metastable crystal form B of N-(aminoiminomethyl)-2-aminoacetic acid according to the invention can be produced in that N-(aminoiminomethyl)-2-aminoacetic acid is brought to crystallisation in the presence of calcium chloride.

The proportion of calcium chloride (based on the water-free salt) is preferably at least 5 to maximally 50 wt. %, particularly preferably 10 to 40 wt. %. The proportion of calcium chloride relates to the total weight of the solution used for the crystallisation of the N-(aminoiminomethyl)-2-aminoacetic acid here.

The calcium chloride (based on to the water-free salt) can also preferably be used in a quantity of at least 5 wt. % and at most 50 wt. % (in relation to the total weight of the solution). The calcium chloride can preferably be used in a quantity of at least 7 wt. %, more preferably at least 10 wt. %, particularly preferably at least 15 wt. % and especially preferably at least 20 wt. %, wherein at most 50 wt. % (each in relation to the total weight of the solution) are also preferably used. At the same time the calcium chloride can be used in a quantity of at most 50 wt. %, more preferably of at most 45 wt. % and especially preferably of at most 40 wt. % (each in relation to the total weight of the solution).

A method for producing a thermodynamically metastable crystal modification of N-(aminoiminomethyl)-2-aminoacetic acid is therefore also a subject of the present invention in that N-(aminoiminomethyl)-2-aminoacetic acid is crystallised from a solution containing 5 to 50 wt. % calcium chloride, preferably 5 to 40 wt. % calcium chloride, preferably 10 to 40 wt. % calcium chloride.

The method can be carried out:
a) through recrystallisation of N-(aminoiminomethyl)-2-aminoacetic acid of any crystal structure from a calcium chloride-containing solvent, or
b) through synthesis of N-(aminoiminomethyl)-2-aminoacetic acid, preferably through conversion of glycine with cyanamide in a calcium chloride-containing solvent.

The method can preferably be carried out in that the N-(aminoiminomethyl)-2-aminoacetic acid is crystallised within a temperature range of −40 to 100° C.

Particularly preferred is a method where N-(aminoiminomethyl)-2-aminoacetic acid is crystallised with a cooling rate within a range of 0.01 to 5 K/min within a temperature range of −40 to 100° C.

Water, alcohols, esters, nitriles, ketones or mixtures of these solvents can preferably be used as solvents. Aqueous or water-containing solvent mixtures are preferred, especially preferred is water.

It has further surprisingly been found that the presence of calcium chloride very clearly increases the solubility of N-(aminoiminomethyl)-2-aminoacetic acid. This, amongst other things, can also be of advantage if more highly concentrated solutions or liquid formulations of N-(aminoiminomethyl)-2-aminoacetic acid are desired.

N-(aminoiminomethyl)-2-aminoacetic acid is dissolved in the said calcium chloride containing-solvent or solvent mixture either according to a) for saturation, or according to b) generated from glycine and cyanamide through a synthesis reaction, so that saturation point is reached as the reaction proceeds. According to the method of the invention the crystal nucleus formation and crystallisation preferably takes place in form B, wherein the presence of calcium chloride is considered essential to the invention.

N-(aminoiminomethyl)-2-aminoacetic acid of the form B can therefore preferably be produced through
a1) cooling crystallisation of a solution saturated at an increased temperature until oversaturation is reached, or
a2) evaporating part of the solvent at a substantially constant temperature until oversaturation is reached,
or
b) reaction whilst forming N-(aminoiminomethyl)-2-aminoacetic acid, wherein the saturation point of the solubility is exceeded,
so that N-(aminoiminomethyl)-2-aminoacetic acid form B is crystallised.

In all cases conventional stirred reactors are preferably used. The use of complex process apparatuses is not required.

The preferred temperature range for the method according to a1), a2) or b) is −40 to 110° C., particularly preferably −20 to 100° C.

For the method according to a1) the dissolution temperature is preferably 40 to 110° C., the crystallisation temperature preferably −40 to 40° C.

Methods according to a2) are preferably carried out within a temperature range of 30 to 100° C.

Methods according to b) are preferably carried out within a temperature range of between 60 and 100° C.

Following complete crystallisation of the desired N-(aminoiminomethyl)-2-aminoacetic acid form B the crystallised product is preferably filtered out through filtration, for example by means of a centrifuge, nutsch-type pressure filters, band filters or a filter press. To remove excess calcium chloride post-washing is preferably carried out with the above mentioned solvent or solvent mixture. Water is preferably used for washing, wherein the temperature of the washing water is preferably 0 to 50° C.

It is of course possible for improving the economy of the method to return the mother liquor obtained from separating the N-(aminoiminomethyl)-2-aminoacetic acid of crystal form B into the process, possibly whilst adjusting the concentration of calcium chloride, for example through evaporation. Following drying, preferably within a temperature range of 40 to 100° C., the method according to the invention supplies a dry, flowable, grainy product consisting of radially radiating, polygonal or rounded aggregates. The crystal aggregates have an external dimension of 150 to 3000 µm, preferably 300 to 1500 µm and a dust content (i.e. particle content that is smaller than 63 µm) of less than 5 wt. %, particle sizes are mesh sizes).

The N-(aminoiminomethyl)-2-aminoacetic acid form B produced in this way has a high purity, typically >99.0%, is easy to handle and displays very little mechanical wear. Thanks to these properties the crystal form B of N-(aminoiminomethyl)-2-aminoacetic acid is particularly well suited for the above mentioned purposes, in particular as a nutritional additive or as a pharmaceutical active substance.

A further object of the present invention is therefore the use of the thermodynamically metastable crystal modification of N-(aminoiminomethyl)-2-aminoacetic acid as described herein for producing an animal feed additive as well as an animal feed additive comprising a thermodynamically metastable crystal modification of N-(aminoiminomethyl)-2-aminoacetic acid as described herein. The animal feed additive is in particular suitable for feeding poultry.

The following examples will illustrate the nature of the invention in more detail.

EXAMPLES

X-Ray Powder-Diffractometric Measurement

Within the scope of the present examples x-ray powder-diffractometric measurements were carried out using a powder diffractometer Bruker D2 Phaser with theta/2theta geometry, a LYNXEYE detector, Cu-K$\alpha_1$ radiation with the wavelength 1.5406 Å with an acceleration voltage of 30 kV and an anode current of 10 mA, a nickel filter and a increment of 0.02°. The samples provided for investigation were ground in an agate mortar pressed onto the sample plate according to manufacturer's instructions, and the surface smoothed.

Single Crystal x-Ray Structure Analysis

Figure 7:
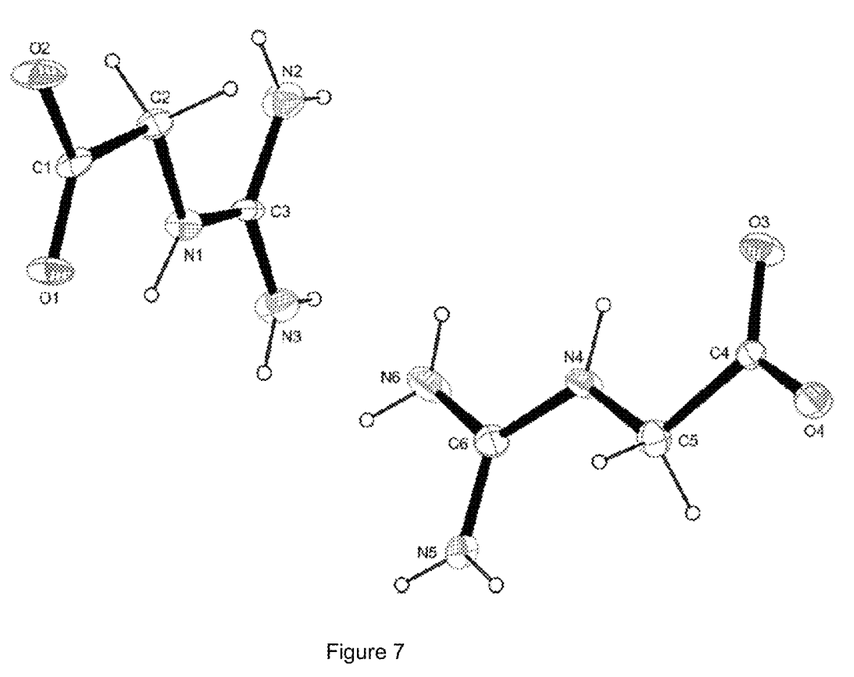
FIG. 7: an illustration of the two crystallographically independent molecules N-(aminoiminomethyl)-2-aminoacetic acid from the single crystal x-ray structure analysis.
Figure 8:
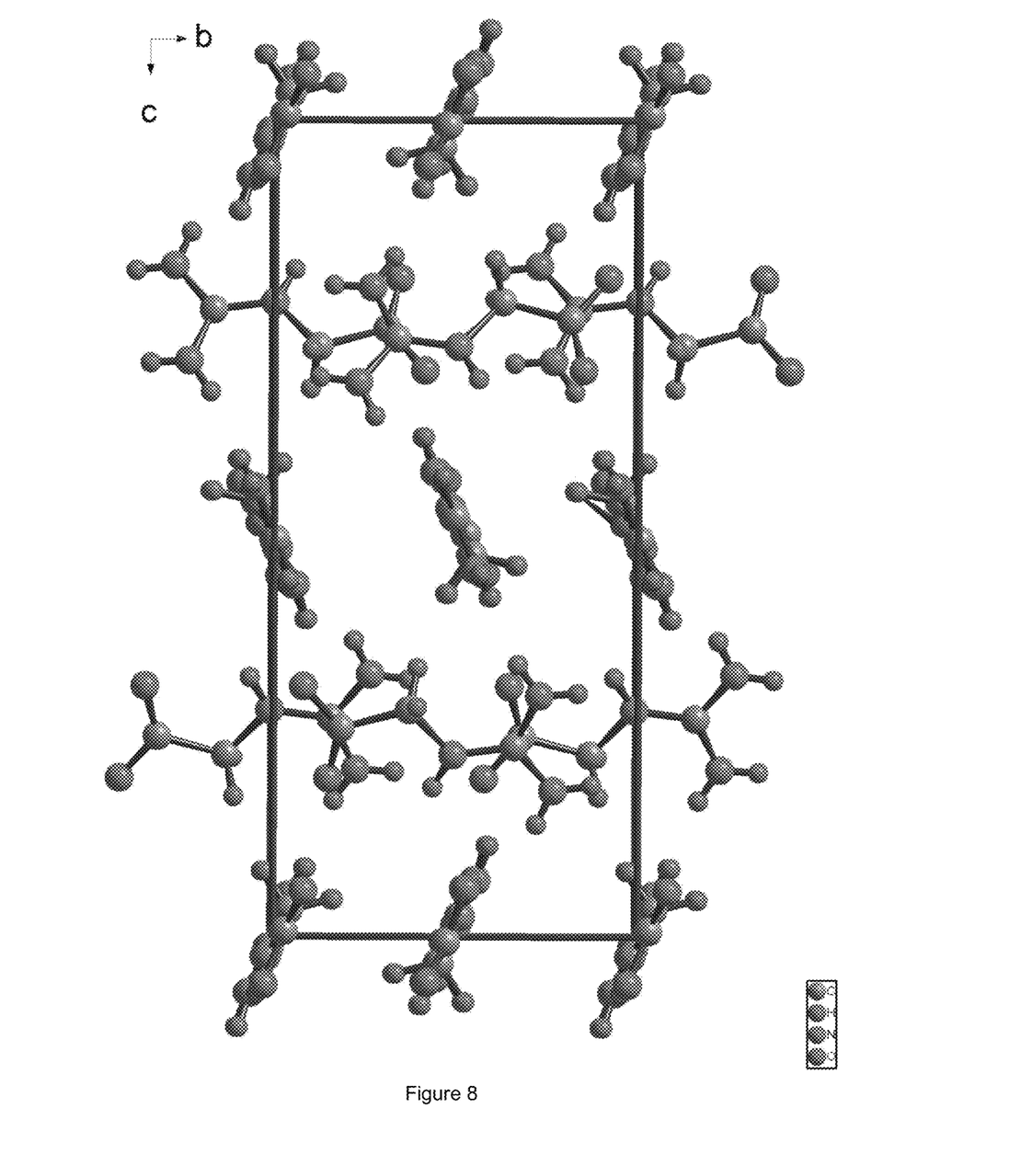
FIG. 8: an illustration of the packaging of the molecules of N-(aminoiminomethyl)-2-aminoacetic acid in the crystal structure. The viewing direction is along the a-axis. Molecule chains parallel to the a- and b-axis that are independent from and arranged vertically to each other and are bound via H-bridges can be clearly seen. These chains are stacked along the c-axis.

A suitable crystal was produced through evaporating an aqueous solution of N-(aminoiminomethyl)-2-aminoacetic acid in the presence of calcium chloride. The single crystal measurement was carried out at 105 Kelvin on a crystal with the dimensions 0.02*0.02*0.09 mm, using monochromatic Mo-K$\alpha$ (molybdenum-K-alpha) radiation with the wavelength 0.71073 Å, using a dual-circuit diffractometer Bruker D8 Venture TXS. The refinement of the x-ray crystal data using 2072 independent reflexes was carried out with the method of the smallest error squares up to an R value ($F_{obs}$) of 0.0381. The Position of the NH- and OH-hydrogen atoms was refined, which fixes the CH-hydrogen atoms in the calculated position. The result of the x-ray single crystal structure analysis is demonstrated in FIGS. 7 and 8. A powder diffractogram recalculated from the single crystal structure analysis agreed exactly with the measured powder diffractogram according to FIG. 2.

Example 1 (Comparison)—Recrystallisation of N-(Aminoiminomethyl)-2-Aminoacetic Acid from Water 400 g water was provided at 80° C. and a total of 11.66 g N-(aminoiminomethyl)-2-aminoacetic acid with a content of 99.0%, here in crystal form A, dissolved in the same spoon by spoon, wherein the solubility limit was exceeded with the last portion. This was filtered at 80° C., a further 100 g water was added to the filtrate and heated to 80° C. A barely saturated clear solution was formed. Slow cooling to 20° C. over 4 hours crystallised N-(aminoiminomethyl)-2-aminoacetic acid. The precipitated crystals were filtered out and dried in a vacuum at 60° C. 6.51 g of N-(aminoiminomethyl)-2-aminoacetic acid with a content of 99.1% was obtained.

The obtained product is present in the form of fine needle-shaped crystals. The fine needle-shaped crystals were microscopically examined (see FIG. 3). An x-ray powder-diffractometric measurement resulted in the powder diffractogram shown in FIG. 1, which indicates the well-known crystal form A.

Example 2 (According to the Invention)—Recrystallisation of N-(Aminoiminomethyl)-2-Aminoacetic Acid from a 30% Calcium Chloride Solution A 30% solution was produced from 150 g water-free calcium chloride and 350 g water. N-(aminoiminomethyl)-2-aminoacetic acid of the same composition as in example 1 (i.e. 99.0% content, crystal form A) was added spoon by spoon to 400 g of this solution at 80° C. Only at an added quantity of 74.28 g was the solubility limit exceeded. The low solids content was filtered out at 80° C., not washed, the filtrate admixed with the remaining 100 g of the 30% solution of calcium chloride, and stirred at 80° C. for 1 hour. A clear, colourless solution was obtained. Slow cooling to 20° C. over 4 hours crystallised N-(aminoiminomethyl)-2-aminoacetic acid. The precipitated crystal aggregates were filtered out, washed 3 times with water at 20° C. and dried at 60° C. 46.42 g N-(aminoiminomethyl)-2-aminoacetic acid with a content of 99.2% was obtained. The obtained quantity is therefore 7 times greater than in example 1, which is due to the solubility of N-(aminoiminomethyl)-2-aminoacetic acid that is strongly increased through calcium chloride.

An analogously recorded powder diffractogram (see FIG. 2) showed the previously unknown crystal form B. The polygonal, rounded crystal aggregates were microscopically examined (see FIG. 4).

Example 3 (According to the Invention)—Recrystallisation of N-(Aminoiminomethyl)-2-Aminoacetic Acid from a 15% Calcium Chloride Solution Example 2 was repeated analogously with 500 g of a 15% calcium chloride solution produced from 75 g water-free calcium chloride and 425 g water. The saturation limit was reached with 42.7 g N-(aminoiminomethyl)-2-aminoacetic acid in 400 g of this solvent mixture at 80° C. Following addition of the remaining 100 g of solvent, crystallisation of the initially clear solution, filtration, washing and drying, 27.2 g N-(aminoiminomethyl)-2-aminoacetic acid with a content of 99.2% was obtained.

The powder diffractogram of the spherical crystal aggregates indicated the sole presence of form B. The spherical, radially radiating aggregates were microscopically examined (see FIG. 5).

Example 3a (According to the Invention)—Recrystallisation of N-(Aminoiminomethyl)-2-Aminoacetic Acid from a 10% Calcium Chloride Solution Example 2 was repeated analogously with 500 g of a 10% calcium chloride solution produced from 50 g water-free calcium chloride and 450 g water. The saturation limit was reached with 29.4 g N-(aminoiminomethyl)-2-aminoacetic acid in 400 g of this solvent mixture at 80° C. Following addition of the remaining 100 g of solvent, crystallisation of the initially clear solution, filtration, washing and drying, 23.5 g N-(aminoiminomethyl)-2-aminoacetic acid with a content of 99.3% was obtained.

The powder diffractogram indicated the presence of a mixture of crystal form A and crystal form B. The ration of both polymorphs was approx. 1:1.

Example 3b (Comparison)—Recrystallisation of N-(Aminoiminomethyl)-2-Aminoacetic Acid from a 1% Calcium Chloride Solution Example 2 was repeated analogously with 500 g of a 1% calcium chloride solution produced from 5 g water-free calcium chloride and 495 g water. The saturation limit was reached with 13.4 g N-(aminoiminomethyl)-2-aminoacetic acid in 400 g of this solvent mixture at 80° C. Following addition of the remaining 100 g of solvent, crystallisation of the initially clear solution, filtration, washing and drying, 11.0 g N-(aminoiminomethyl)-2-aminoacetic acid with a content of 99.4% was obtained.

The powder diffractogram of the fine needle-shaped crystal aggregates indicated the sole presence of form A.

Depending on the calcium chloride concentration the creation of form A or form B can therefore be influenced. The solubility (i.e. saturation limit) of N-(aminoiminomethyl)-2-aminoacetic acid increases strongly with the calcium chloride concentration.

Example 4 (Comparison)—Recrystallisation of N-(Aminoiminomethyl)-2-Aminoacetic Acid from a 50% Solution of Magnesium Chloride Hexahydrate Example 2 was repeated analogously with 500 g of a solution produced from 250 g magnesium chloride hexahydrate and 250 g water. The saturation limit was reached with 76.6 g N-(aminoiminomethyl)-2-aminoacetic acid in 400 g of this solvent mixture at 80° C. Following addition of the remaining 100 g of solvent, crystallisation, filtration, washing and drying, 49.1 g N-(aminoiminomethyl)-2-aminoacetic acid with a content of 99.1% was obtained.

The powder diffractogram of the fine needle-shaped crystal aggregates obtained indicated the sole presence of form A. $MgCl_2$, which is very similar to $CaCl_2$, thus does not affect the crystallisation of N-(aminoiminomethyl)-2-aminoacetic acid in form B even though the solubility of N-(aminoiminomethyl)-2-aminoacetic acid is strongly increased in a similar way by the presence of the salt.

Example 5 (Comparison)—Synthesis of N-(Aminoiminomethyl)-2-Aminoacetic Acid from Glycine and Cyanamide in Aqueous Solution 112.6 g (1.5 mol) glycine was dissolved in 300 g water. The solution was admixed with 21.6 g (0.27 mol) of 50% caustic soda, wherein a pH value of 8.4 resulted. At 80° C. over a period of 4 hours a solution of 42.04 g (1.0 mol) cyanamide dissolved in 42 g water was added. The post-reaction took place for a further hour at 80° C. The obtained suspension was cooled to 20° C., filtered, washed with water and dried at 60° C. 100.6 g N-(aminoiminomethyl)-2-aminoacetic acid with a content of 99.1% was obtained. The yield was 85.9%.

A powder diffractogram of the obtained fine needle-shaped crystals indicated the sole presence of form A.

Example 6 (According to the Invention)—Synthesis of N-(Aminoiminomethyl)-2-Aminoacetic Acid from Glycine and Cyanamide in a 33% Calcium Chloride Solution A solution was produced from 100 g water-free calcium chloride and 200 g water. 112.6 g (1.5 mol) glycine was dissolved in this and a pH value of 8.4 set with 21.6 g (0.27 mol) of 50% caustic soda. At 80° C. over a period of 4 hours a solution of 42.04 g (1.0 mol) cyanamide dissolved in 42 g water was added. The post-reaction took place for a further hour at 80° C. The obtained suspension was cooled to 20° C., filtered, washed with water and dried at 60° C. 99.3 g N-(aminoiminomethyl)-2-aminoacetic acid with a content of 99.2% was obtained. The yield was 84.8%.

A powder diffractogram of the obtained rounded crystal aggregates of radially radiating individual crystals indicated the sole presence of form B.

Example 6a (According to the Invention)—Synthesis of N-(Aminoiminomethyl)-2-Aminoacetic Acid from Glycine and Cyanamide in a 15% Calcium Chloride Solution A solution was produced from 45 g water-free calcium chloride and 255 g water. 112.6 g (1.5 mol) glycine was dissolved in this and a pH value of 8.4 set with 21.5 g (0.27 mol) of 50% caustic soda. At 80° C. over a period of 4 hours a solution of 42.04 g (1.0 mol) cyanamide dissolved in 42 g water was added. The post-reaction took place for a further hour at 80° C. The obtained suspension was cooled to 20° C., filtered, washed with water and dried at 60° C. 99.6 g N-(aminoiminomethyl)-2-aminoacetic acid with a content of 99.3% was obtained. The yield was 84.5%.

A powder diffractogram of the obtained crystals indicated that a mixture of form A and form B was present wherein form B represented by far the largest proportion.

Example 6b (Comparison)—Synthesis of N-(Aminoiminomethyl)-2-Aminoacetic Acid from Glycine and Cyanamide in a 1% Calcium Chloride Solution A solution was produced from 3 g water-free calcium chloride and 297 g water. 112.6 g (1.5 mol) glycine was dissolved in this and a pH value of 8.4 set with 21.4 g (0.27 mol) of 50% caustic soda. At 80° C. over a period of 4 hours a solution of 42.04 g (1.0 mol) cyanamide dissolved in 42 g water was added. The post-reaction took place for a further hour at 80° C. The obtained suspension was cooled to 20° C., filtered, washed with water and dried at 60° C. 100.1 g N-(aminoiminomethyl)-2-aminoacetic acid with a content of 99.2% was obtained. The yield was 84.8%.

A powder diffractogram of the obtained crystals indicated that only form A was present.

Even if N-(aminoiminomethyl)-2-aminoacetic acid is generated through reaction between glycine and cyanamide, the resulting crystal form can be controlled through the presence of different concentration of calcium chloride.

Example 7—Physical Chemical Characterisation N-(Aminoiminomethyl)-2-Aminoacetic Acid of Form A and Form B 7.1 Melting or Decomposition Point A Mettler DSC 3+ unit with a 40 µl aluminium pan was used for Dynamic Differential Scanning Calorimetry (DSC). The heating rate was 10 Kelvin per minute within a temperature range of 30 to 350° C. Approx. 1.4 mg each of the products from example 1 and 2 was weighed into the aluminium pan and measured at atmospheric pressure (960 mbar at a height position of 500 m over NN).

The sample from example 1 (=N-(aminoiminomethyl)-2-aminoacetic acid of the form A) showed an onset (turning point of the melting graph projected onto the base line) of 280.5° C. and a peak temperature of the melting graph of 286.3° C. The total endothermic melt heat was 887 J/g. The product discoloured during melting from white to brown.

The sample from example 2 (=N-(aminoiminomethyl)-2-aminoacetic acid form B) was analogously measured. It showed an onset of 272.5° C. and a peak of 280.4° C., the melt heat was 860 J/g, the discolouration was identical.

Form B therefore melts at approx. 6 to 8 Kelvin lower than form A and has a 27 J/g lower melt heat or a 27 J/g higher lattice energy, respectively. In other words, 27 J/g less energy is required for form B than is needed for form A to reach an identical energy melt condition. Form B thus constitutes a metastable crystal form or an energetically higher positioned polymorph of N-(aminoiminomethyl)-2-aminoacetic acid under normal pressure and temperature conditions.

7.2 Determination of Water Solubility 100 g water of 5° C. was provided. The product from example 1 (=N-(aminoiminomethyl)-2-aminoacetic acid form A) was dissolved therein up to saturation, and the dissolved quantity determined through back weighing. The temperature was then increased to 20° C. and as much as required of the sample was added to reach saturation point. The same was repeated at further temperatures with a maximum at 95° C. An analogue measurement was carried out with the product from example 2 (=N-(aminoiminomethyl)-2-aminoacetic acid form B). The obtained solubility data for both products are graphically summarised in FIG. 6.

Both crystal forms of N-(aminoiminomethyl)-2-aminoacetic acid dissolve better in water as the temperature increases. The N-(aminoiminomethyl)-2-aminoacetic acid form B according to the invention dissolves by around 20% better than the known form A at any temperature.

7.3 Determination of Density

Crystals of N-(aminoiminomethyl)-2-aminoacetic acid form A from example 1 were introduced to tetrachloromethane at 20° C., where they floated on the surface. A drop-by-drop addition of dichloromethane lowered the density of the liquid medium until the crystals just started to float in the liquid without rising and without sinking to the bottom. The density of the liquid phase was determined in a pyknometer. 1.50 g/cm$^3$ was measured.

Crystals of the form B from example 2 were treated in the same way. The density at 20° C. was determined as 1.41 g/cm$^3$.

Form B therefore has 6% less density than form A. This correlates with the above mentioned lower lattice energy of form B. The measured crystal densities also agree with the x-ray crystal data calculated from the respective lattice constants.

7.4 Determination of Dust Content

The product from example 1 was sieved through a sieve with a mesh width of 63 µm (equals a 230 mesh—mesh size). A 46 wt. % fine content was obtained. The sample from example 2 consisting of polygonal, rounded crystal aggregates, was treated in the same way. A fine content of below 3 wt. % was determined here. Low-dust, and thus safe-to-handle materials should have a dust content (i.e. grain content <63 µm) of below 10%. The product from example 2 (N-(aminoiminomethyl)-2-aminoacetic acid of the crystal form B) fulfils this, whilst comparison example 1 (N-(aminoiminomethyl)-2-aminoacetic acid of the crystal form A) does not fulfil it.

7.5 Determination of Angle of Repose

The product from example 1, consisting of needle-shaped crystals matted to each other, was poured through a funnel onto a level surface with a device according to DIN ISO 4324. After removing the funnel the slope angle of the obtained cone was determined with an angle measuring means. It was approx. 45°. N-(aminoiminomethyl)-2-aminoacetic acid form A therefore displays poor flow characteristics. The grainy product from example 2 was measured in the same way. A slope angle of approx. 25° was obtained here. N-(aminoiminomethyl)-2-aminoacetic acid form B therefore displays excellent flow characteristics.

7.6 Determination of Bulk Density

A weighed-in quantity of the product from example 1 was placed in a measuring cylinder and partially compacted by firmly tapping the same on the laboratory table twice. The bulk density was determined as 0.37 g/cm$^3$ from the filling height of the measuring cylinder. The product from example 2 was treated in the same way. A bulk density of 0.62 g/cm$^3$ was determined here. N-(aminoiminomethyl)-2-aminoacetic acid of the form B therefore has a clearly increased bulk density, which is of advantage for the packing, transport and handling of the product.

7.7 Thermal Stability of N-(Aminoiminomethyl)-2-Aminoacetic Acid Form B a) N-(aminoiminomethyl)-2-aminoacetic acid form B from example 2 was placed in a drying cabinet at 120° C. for 6 hours. The crystal form was then determined by means of x-ray powder diffractometry. It remained unchanged in a pure crystal form B.

b) N-(aminoiminomethyl)-2-aminoacetic acid form B from example 2 was moistened with 20% water, incubated in a closed vessel at 65° C. for 6 hours, then dried. The x-ray powder diffractogram showed no change, form B remained stable.

c) N-(aminoiminomethyl)-2-aminoacetic acid form B from example 2 was turned into a 10% suspension in water. This suspension was stirred for 2 hours at 80° C. It was then cooled, the solids filtered out and dried. X-ray powder diffractometry showed that a mixture of crystal forms A and B was present.

d) N-(aminoiminomethyl)-2-aminoacetic acid form B from example 2 was dissolved in water at 80° C., mostly crystallised once more through cooling the solution, filtered and dried. X-ray powder diffractometry resulted in a pure crystal form A.

N-(aminoiminomethyl)-2-aminoacetic acid form B is thus very stable in solid form, but has the tendency to transfer into crystal form A via the aqueous solution. This characteristic also confirms the metastable crystal structure of form B.

Example 8—Synthesis of N-(Aminoiminomethyl)-2-Aminoacetic Acid According to Prior Art, in which Calcium is Present—DE 964 590 B Note: The calcium cyanamide used according to DE 964 590 B has a content of just 53%; this equals 15.9% N. In the following example calcium cyanamide with a content of 68.6% was used; this equals 24% N. The quantity used was adapted accordingly.

154.5 g technical calcium cyanamide with a content of 68.6% CaNCN was suspended in 800 g water. At 20° C. a mixture of 191.6 g of 96% sulphuric acid and 300 g water was added, wherein cyanamide was transformed into a solution and calcium sulfate precipitated from the solution and a pH value of 7.5 was obtained. Calcium sulfate and other insoluble components were filtered out and the filtrate set to a pH of pH 4.9 with a little sulphuric acid. The obtained solution was vaporised to a total volume of 200 cm$^3$ under a reduced pressure of approx. 10 mbar. Further precipitated calcium sulfate was filtered out. The obtained aqueous cyanamide solution has a cyanamide content of 26.4% and a calcium content of 0.56 g/litre. (Note: equals a cyanamide yield of 95% and a gypsum solubility of 2.4 g/l).

This cyanamide solution was admixed with 30 g glycine and set to a pH of 9.4 with 19.8 g of 50% aqueous caustic soda. The reaction mixture was heated to 95° C. for 1.5 hours and then cooled to room temperature overnight. Precipitated N-(aminoiminomethyl)-2-aminoacetic acid as well as any dicyandiamide also created was filtered out, the filter residue was taken in 180 g water, leached out at 50° C. for two hours, filtered at 50° C. and washed with water. After drying at 60° C., 38.4 g N-(aminoiminomethyl)-2-aminoacetic acid was obtained. The yield was 82% in relation to the glycine used.

X-ray powder diffractometry showed that N-(aminoiminomethyl)-2-aminoacetic acid had been created only in crystal form A.

The invention claimed is:

1. A thermodynamically metastable crystal form of N-(aminoiminomethyl)-2-aminoacetic acid, wherein the crystal form in the x-ray powder diffractogram of the crystal form shows the strongest reflex bands at 2Θ=20.2°, 23.3°, 23.8° and 25.3° at a measuring accuracy of +/−0.2° when using Cu-K$\alpha_1$ radiation.

2. The crystal form according to claim 1, wherein the crystal form has the orthorhombic space group $P2_12_12_1$ with Z=8 with the lattice constants a=7.7685 Å, b=7.7683 Å and c=17.4261 Å at 105 Kelvin and a measuring accuracy of +/−0.001 Å.

3. The crystal form according to claim 2, wherein the crystal form has a cell volume of 1052 Å$^3$ at 105 Kelvin.

4. The crystal form according to claim 1, wherein the crystal form has an experimental crystal density of 1.41 g/cm$^3$+/−0.03 g/cm$^3$ at 20° C.

5. The crystal form according to claim 1, wherein the crystal form has an endothermic melt heat within a range of 850 to 870 J/g.

6. The crystal form according to claim 1, wherein the crystal form has a decomposition point within a range of 270 to 275° C.

7. A method for producing a thermodynamically metastable crystal form of N-(aminoiminomethyl)-2-aminoacetic acid according to claim 1, wherein N-(aminoiminomethyl)-2-aminoacetic acid is crystallized from a solution containing 5 to 50 wt. % calcium chloride.

8. The method according to claim 7, wherein N-(aminoiminomethyl)-2-aminoacetic acid is crystallized from a solution containing 10 to 40 wt. % calcium chloride.

9. The method according to claim 7, wherein N-(aminoiminomethyl)-2-aminoacetic acid is crystallized within a temperature range of −40 to 100° C.

10. The method according to claim 7, wherein N-(aminoiminomethyl)-2-aminoacetic acid is crystallized with a cooling rate within a range of 0.01 to 5 K/min within a temperature range of −40 to 100° C.

11. The method according to claim 7, wherein the solution contains a solvent from the group of water, alcohols, esters, nitriles, ketones or mixture of the same as a solvent.

12. An animal feed additive comprising a thermodynamically metastable crystal form of claim 1.

* * * * *